United States Patent [19]

Kojima et al.

[11] Patent Number: 5,110,442
[45] Date of Patent: May 5, 1992

[54] REINFORCED ELECTROLYTE FUNCTION ELEMENTS

[75] Inventors: Takao Kojima; Hiroyuki Ishiguro; Yoshiki Kawachi; Tetsusyo Yamada, all of Nagoya, Japan

[73] Assignee: NGK Spark Plug Co., Ltd., Nagoya, Japan

[21] Appl. No.: 319,043

[22] Filed: Mar. 6, 1989

Related U.S. Application Data

[63] Continuation of Ser. No. 947,821, Dec. 30, 1986, abandoned, which is a continuation-in-part of Ser. No. 749,467, Jun. 27, 1985, abandoned, and a continuation-in-part of Ser. No. 749,457, Jun. 27, 1985, abandoned.

[30] Foreign Application Priority Data

Jun. 27, 1984 [JP] Japan .................. 59-130937
Jun. 27, 1984 [JP] Japan .................. 59-130938
Aug. 21, 1984 [JP] Japan .................. 59-172352

[51] Int. Cl.$^5$ ..................... G01N 27/409
[52] U.S. Cl. ..................... 204/426; 204/429; 264/61; 427/126.4
[58] Field of Search ........... 204/15, 421–429, 204/153.18

[56] References Cited

U.S. PATENT DOCUMENTS

| | | | |
|---|---|---|---|
| 3,935,089 | 1/1976 | Togawa et al. | 204/429 |
| 4,224,113 | 9/1980 | Kimura et al. | 204/15 |
| 4,304,652 | 12/1981 | Chiba et al. | 204/425 |
| 4,334,974 | 6/1982 | Muller et al. | 204/425 |
| 4,449,919 | 5/1984 | Takikawa et al. | 204/426 |
| 4,476,008 | 10/1984 | Sano et al. | 204/425 |
| 4,502,939 | 3/1985 | Holfelder et al. | 204/429 |
| 4,663,215 | 5/1987 | Dubuisson et al. | 428/209 |

FOREIGN PATENT DOCUMENTS

0008175 2/1980 European Pat. Off. .
59-166854 9/1984 Japan .

*Primary Examiner*—T. Tung
*Attorney, Agent, or Firm*—Fish & Richardson

[57] ABSTRACT

A zirconia-base solid electrolyte function element comprising a zirconia-base solid electrolyte substrate, wherein a reinforcing layer is formed directly on each side of said zirconia-base solid electrolyte substrate, the ratio of the shrinkage modulus to the zirconia-base electrolyte substrate to the reinforcing layers is 1.01 to 1.08, and the substrate and the reinforcing layers have been sintered simultaneously.

14 Claims, 4 Drawing Sheets

| | |
|---|---|
| thickness of 1 | 0.65 mm |
| thickness of 2 (minimum) | 10 μm |
| thickness of 4 (Pt) | 25 μm |
| width of 4 | 1 mm |

FIG.7

REINFORCED ELECTROLYTE FUNCTION ELEMENTS

This application is a continuation of U.S. application Ser. No. 947,821, filed Dec. 30, 1986, now abandoned, which is a Continuation In Part Application of U.S. patent applications Ser. No. 749,467 filed on Jun. 27, 1985 and Ser. No. 749,457 filed on Jun. 27, 1985, both herewith abandoned.

FIELD OF THE INVENTION

This invention relates to a sintered body serving as a plate-like solid electrolyte, which is used for fuel cells, various sensors and the like.

Furthermore, this invention relates to a plate-like zirconia solid electrolyte function element and, more particularly, to a plate-like zirconia solid electrolyte function element in which it is very unlikely that breaking accidents may arise during processing or assembling, or in use, and the insulating properties of the lead portion is considerably improved over the conventional elements.

BACKGROUND OF THE INVENTION

In general, the functions that solid electrolytes have are largely classified into three functions, electromotive function due to an activity difference, selective ion transmission function and uneven ion distribution function. Referring to the electromotive function out of these functions, a reference substance having known activity and a substance to be measured are allowed to be in contact with one side and the opposite side of a plate-like solid electrolyte respectively. The activity of the substance to be measured can then be determined from an electromotive force value produced therebetween.

In recent years, rapidly increasing attention is paid to ceramic sensors making use of solid electrolytes, and such sensors are now used in large fields. In particular, oxygen sensors making use of zirconia ceramics are of sharp responsiveness and are stable in the electromotive force, so that a partial oxygen pressure can be detected over an extensive range. Besides, those oxygen sensors have the advantage that they can stand up to high temperatures. For those reasons, they are now used in various fields in which energy saving, prevention of environmental pollution, etc. are intended, including combustion controls for automobile engines and detectors for partial or incomplete combustion in domestic gas water heaters.

In the oxygen sensors to which the electromotive function of solid electrolytes, for instance, $ZrO_2$-base solid electrolytes are formed into a plate-like shape, and are used in a state where $ZrO_2$ is partially stabilized by the addition of small amounts of stabilizers such as $Y_2O_3$. For instance, the amount of $Y_2O_3$ to be added has been usually about 4.5 mol % to maintain the mechanical strength at a given value or higher.

However, if it is intended to increase the mechanical strength by reducing the amount of $Y_2O_3$, a bending strength reaches as high as 50 kg/mm$^2$ or more, but there is a drop of electrical conductivity so that it insufficiently functions as the resistor of the $ZrO_2$ element. On the contrary, the addition of $Y_2O_3$ in an amount exceeding 6 mol % results in improvements in electrical conductivity, but causes a reduction of a bending strength to 30 kg/mm$^2$ or less.

Generally, the sensing element of oxygen sensors is constructed by attaching platinum electrodes to both sides of a wholly or partially stabilized zirconia solid electrolyte-base thin plate. However, since it has a thickness on the order of about several millimeters, it is very likely that it may be easily broken during processing or assembling, or in use. Thus, there is a demand for the development of detection elements excelling in mechanical strength.

Besides, in general, one means for enhancing the strength of sintered bodies involves the addition of the predetermined amount of impurities to the base material, whereby the growth of grains during sintering is inhibited. Another means for strengthening sintered bodies involves the coating of particles on the surface of the formed base material mass, said particles having an ion radius larger than that of said base material mass, thereby to cause substitution and solid-solution formation for producing compression stress in the surface of said base material mass.

According to the reinforcing manner in which the aforesaid impurities are added, however, the strength of the base material may be affected depending upon the type of said impurities. This needs time-consuming examination of the type of impurities. Thus, such a manner for reinforcing sintered bodies cannot be said to be a generally applicable reinforcing treatment without difficulty. According to another reinforcing manner to form the coating layers, the compression stress varies depending upon the type of the coating materials, viz, the degree of substitution and solid solution formation with respect to the base material, with the resulting variations in strength. This leads to the deficiency of reinforced stability and, in some cases, may result in the formation of cracks on the surface of sintered bodies.

Furthermore, there are oxygen sensors which is constructed by laminating $Al_2O_3$ layer on the surface of zirconia solid electrolyte substrate, such as U.S. Pat. No. 4,502,939 or U.S. Pat. No. 4,334,974. However, those solid electrolyte function elements have still not satisfactory strength.

SUMMARY OF THE DISCLOSURE

One object (first aspect) of the present invention is to provide wholly or partially stabilized zirconia-base sintered bodies which function satisfactorily as solid electrolytes and have improved mechanical strength.

It is another object (second aspect) of the present invention to provide a process for the production of the sintered bodies of the same type as mentioned for the first aspect.

A further object (third aspect) of the present invention is to provide reinforced zirconia-base electrolyte function elements having improved mechanical strength and excellent performance, and a process for the production thereof.

Still other objects will become apparent in the entire disclosure.

According to the first aspect of the present invention there is provided a partially or wholly stabilized zirconia-base reinforced sintered body characterized in that a plate-like sintered substrate of a partially or wholly stabilized zirconia-base sintered mass provided with on each side thereof an alumina-base protective layer having a given thickness. The thickness ratio of each alumina-base protective layer to said plate-like sintered substrate should be 1/100 to 25/100.

According to a second aspect of the present invention there is provided a process for the production of partially or wholly stabilized zirconia-base reinforced sintered bodies comprising:

providing a green alumina protective layer on each side of a plate-like zirconia-base substrate, and sintering the resultant mass so as to simultaneously sinter the substrate and the protective layers to form an integral sintered body.

According to a third aspect of the present invention there is provided a plate-like zirconia-base solid electrolyte function element comprising a plate-like zirconia-base solid electrolyte substrate, the substrate including at its free end an electrochemically operable portion provided with an electrode on each side of the substrate, another portion (e.g., another end portion) to be retained, and an arm portion defined by an intermediate portion between the free end and said another portion, characterized in that a reinforcing coating layer is formed on each side of said zirconia-base solid electrolyte substrate, the reinforcing coating layers extending at least from said arm portion to said another portion to be retained, said coating layers being formed of an electrically insulating ceramic material having a shrinkage modulus smaller than that of said zirconia-base solid electrolyte substrate.

The insulating ceramic material is preferably alpha-alumina. It is preferred that the zirconia-base solid electrolyte is wholly or partially stabilized primarily by yttrium oxide. The ratio of the shrinkage moduli between said zirconia-base electrolyte substrate and the ceramic material forming the coating layers should be 1.01 to 1.08. The thickness ratio of each of said coating layers and said zirconia solid electrolyte plate generally ranges from 1/100 to 25/100. The zirconia-base solid electrolyte substrate may have a thickness of 0.1 to 5 mm (preferably 0.1 to 2 mm). The lead portion may be formed on the surface of said insulating ceramic material. When the substrate is the partially stabilized zirconia (PSZ), the function element has a high strength (e.g. 50 kg/mm$^2$) after ageing at 250° C. for 500 hours, and therefore an excellent low-temperature stability.

PREFERRED EMBODIMENTS

The reinforced sintered body based on partially or wholly stabilized $ZrO_2$ according to the first aspect of the present invention includes a plate-like substrate and $Al_2O_3$-base protective layers of a given thickness, which are applied on each side of the substrate. In the present disclosure, the wording "plate-like" means any profiles such as plates (or sheets), curved plates or other configurations (generally, pipes) formed of such curved plates.

According to the second aspect of the invention, the protective layers and the substrate are simultaneously sintered into a plate-like integral sintered body.

The thickness ratio of one protective layer of $Al_2O_3$ to the $ZrO_2$-base sintered substrate should be 1/100 to 25/100, preferably 1/100 to 20/100, most preferably 5/100 to 15/100. If required, the protective layer may be formed partly or entirely over the plate-like substrate.

According to the foregoing arrangement, it is possible to achieve a mechanical strength higher than that of the sintered body comprising the substrate alone by a factor of twice or more, since the protective layers and the substrate contract integrally, and synergistically interact with each other. According to the present invention, the thus obtained strength exceeds that of the $Al_2O_3$-base layers per se used as the protective layers. This is considered to be due to the fact that the shrinkage moduli (shrinkage modulus = green size/sintered size) of the substrate and the protective layers (coating material) are used in varied combinations upon sintering the substrate onto which the protective layers have been applied. More specifically, to make the shrinkage modulus of the coating material smaller than that of the substrate would mean that the coating material shrinks to a higher degree than the original degree of shrinkage during sintering resulting in further densification, and that there is produced therein a compression stress. It is considered that the higher the difference in the relative ratio of the shrinkage moduli between the coating material and the substrate, the greater the resulting effect, provided that the sintered body must be free from any crack, warpage, etc. Preferably, the ratio of the shrinkage moduli of the substrate to that of the coating material should be in a range of 1.01 to 1.08, more preferably 1.03 to 1.06. The adjustment of the ratio of the shrinkage moduli may be effected preferably in the following manner. In general, zirconia raw material is pre-calcined to an appropriate extent for providing a zirconia-base solid electrolyte substrate (sheet). Thereupon, the calcination temperature should be kept to a considerably lower temperature, and the doctor blade method should be applied for sheet forming. The following is a typical procedure:

Mixing of materials—calcination (1300°–1380° C.)—pulverization—mixing with organic binder—sheet forming by the doctor blade method—screen printing of coating layers—organic binder removal (250° C.)—sintering (about 1550° C.). The protective layer is based on $Al_2O_3$, a preferable example of which is usually alpha-$Al_2O_3$ having a purity of, preferably, no lower than 90%. This is based on the concept that sufficient incorporation of thermally and chemically stable alpha-$Al_2O_3$ is preferable from the very viewpoint of reinforcing layers. Hence, small amounts of other components may be added to alpha-$Al_2O_3$ as the sintering aids or the like purpose. These components may include MgO, CaO, $SiO_2$, $ZrO_2$ or the like. CaO and $SiO_2$ are used mainly as the sintering aids, while $ZrO_2$ and MgO have also grain growth inhibiting effect. Thus CaO and $SiO_2$ are used preferably in no more than 5% by weight.

In the present invention, it is required to make the $ZrO_2$-base substrate integral with the coating material and to use a dense coating material, which leads to the need of sintering the coating material at a temperature at which the substrate is sintered. Therefore, it is preferred that the sintering aids are added to the coating material.

In the following, a preferred embodiment of the process (Second Aspect) for the production of the reinforced sintered bodies will be explained. Stabilizers such as $Y_2O_3$, CaO, MgO, oxides of lanthanide, e.g., $Ce_2O_3$, $Yb_2O_3$, and the like are added to the starting $ZrO_2$ material in the predetermined amount (usually 4 to 10 mol %) for mixing in a ball mill, etc. Sintering aids ($Al_2O_3$, $SiO_2$, MgO) may be present up to 10 mol %, a preferred ones being a composition of $Al_2O_3$ : $SiO_2$ : MgO = 92 : 2 : 4. After drying, the resulting mixture is calcined, and the obtained calcined powder is pulverized to obtain a starting material of the substrate. A binder such as organic binders is added to the substrate, which is formed into a plate-like shape by means of the docotor blade, extrusion, pressing or the like technique to obtain a green shaped substrate based on $ZrO_2$, wherein $ZrO_2$ is partially or entirely stabilized. On the other hand, an organic binder is mixed with the starting $Al_2O_3$ material and the resulting mixture is pasted to obtain a coating material.

The coating material is coated onto each side of the green substrate by means of paste printing or thermocompression bonding, and the resulting product is sintered at 1500° to 1550° C. for 1 to 4 hours in an oxidizing atmosphere, whereby the protective layer-provided plate-like sintered body based on the substrate of partially or wholly stabilized $ZrO_2$ is obtained.

According to the present invention, a bending strength higher than that of a sintered plate-like body of coating material per se (e.g., $Al_2O_3$ can be assured, as noted from the experimental data to be given later.

The substrate of the reinforced sintered body, which can be produced in this manner, has a thickness of, ca. 0.1 to 5 mm, and is thinner than the conventional (single material sheet) product having the same strength by about 20 to 40%.

The third aspect of the present invention will now be explained hereinbelow. As mentioned in the forgoing, The sensing element of an oxygen sensor is generally constructed from a plate based on a partially or wholly stabilized zirconia electrolyte and electrodes (noble metal, e.g., platinum) attached onto both its sides. Due to its thickness of about a few to several millimeters, that element has been apt to failure during processing or assembling or in use.

The present inventors have found out that the problems as mentioned above are solved by the provision of a function element which is mentioned hereinabove in the Summary as the third aspect of the present invention.

The partially or entirely stabilized zirconia reinforced sintered body used for the function element based on the plate-like zirconia solid electrolyte according to the third aspect of the present invention includes a plate-like substrate of partially or enitrely stabilized zirconia and alumina ($Al_2O_3$)-base protective layers (reinforcing coating layers) of a given thickness, which are formed on both sides of the substrate. The protective layers and the substrate are simultaneously sintered to obtain a plate-like integral sintered body. In this case, it is desired that the thickness ratio of the plate-like sintered substrate based on zirconia ($ZrO_2$) to one alumina protective layer is 1/100 to 25/100 (more preferably 1/100 to 20/100, and most preferably 5/100 to 15/100). The protective layer includes at least an arm portion and a retaining portion (to be retained or fixed to a supporting member) and, if required, is formed partially or entirely over the plate-like sintered body except for the electrode portion. The method for forming the protective layers and the reason why the substrate is reinforced thereby have already mentioned in connection with the first and second aspects of the present invention.

In the present disclosure, the term "shrinkage modulus" refers to $l_0/l_1$ wherein $l_0$ denotes the green dimension of unsintered base or coating materials, and $l_1$ stands for the dimension of the base or coating materials after contraction due to sintering.

According to the present invention, there is provided a reinforced plate-like sintered body characterized in that an $Al_2O_3$-base surface layer having a given thickness is disposed partly or entirely over the surface of a base material formed into a plate-like shape; a ratio of the shrinkage modulus $l_0/l_1$ of said base material with respect to the shrinkage modulus $l'_0/l'_1$ of said surface layer is within a range of 1.01 to 1.08, and said base material and said surface layer have been simultaneously sintered.

As mentioned above, the bending strength of the sintered body can be increased to several times (easily 2-3 times) even with a very thin coating layer, if a coating layer having a degree of contraction smaller than that of the base material is applied on the base material. It is possible to reinforce the strength of general plate-like sintered body elements. It is also possible to coat only the portion of the base material to be reinforced in respect of strength without adversely affecting the base material.

Considering the application of such a difference in the contraction due to sintering, (1) a coating layer, which has previously been calcined to decrease the degree of contraction, may be applied, even when the coating layer and the base material are formed of the same type material, and (2) a coating layer having a small degree of contraction may be prepared by the adjustment of grain sizes. Since it is required to unite the coating layer with the base material after sintering, however, it is required to combine the coating layer with the base material in such a manner that peeling of the coating layer is at least prevented.

The plate-like sintered bodies of the present invention are obtained typically in the following manner. An $Al_2O_3$-base surface layer is formed partly or wholly on the surface of a base material formed into a plate-like shape into the predetermined thickness in such a manner that the ratio of the shrinkage moduli of the base material to the surface layer comes within a range of 1.01 to 1.08. Then, the base material (substrate) and the surface layer are simultaneously sintered. Essential herein is the ratio of the shrinkage moduli and simultaneous sintering of the substrate and coating layer (or layers). The coating layer may be applied by simultaneously with base material formation, e.g., co-extrusion or the like.

The present invention is characterized in that a thin coating layer based on alumina ($Al_2O_3$) is simply applied on the surface of the base material, whereby the surface layer is densified, and a compression stress is produced on the surface of the base material, making use of a difference in the contraction between the base material and the $Al_2O_3$-base coating layer material. Various ceramic materials meeting the aforesaid ratio of the shrinkage modulus may be used as the base materials. As to the base materials, preference is given to ceramic materials such as $Al_2O_3$ and $ZrO_2$ including $ZrO_2$-$Y_2O_3$, $ZrO_2$-CaO and like systems.

The surface layer may be applied on one or both sides of the plate-like base material. The thickness of the surface layer should be no higher than 1/5 of the thickness of the base material in the event that it is formed on one side thereof, and should be no higher than ½ (in total) of the thickness of the base material in the event that it is formed on both sides thereof. This is because the coating layer should be contracted according to the contraction of the base material, making use of the contraction difference upon sintering.

The use of this system causes that, the larger the difference in the contraction (including contraction brought about by a difference in the coefficient of expansion in the course of cooling) between the base material and the surface layer during sintering, the higher the strength. However, there is a need of limiting that contraction to such a degree that the sintered bodies cannot suffer cracking, warpage, etc. In view of warpage alone, the surface layers are coated on both sides of the base material formed into a plate-like shape, whereby the strength is reinforced without causing any warpage. From these, the contraction difference during sintering may be selected at one's disposal with respect to the end strength to be desired.

The wording "alumina-base" for the surface layer is herein understood to refer to materials which contain alumina in an amount of no lower than 80 mol %, preferably no lower than 90 mol %, and may include as the impurities $SiO_2$, CaO or the like which usually occur. Positively, those materials may further contain as the grain growth inhibitors or sintering promotors the known MgO, $ZrO_2$, etc. in amounts of within 5 mol %.

The reinforced plate-like sintered bodies of the present invention may be produced by forming, for instance, a partly or wholly stabilized $ZrO_2$-base material into a plate-like shape, and applying $Al_2O_3$-base coating layers having the predetermined thickness on both surfaces thereof. The wording "plate-like" is here understood to refer to flat plates, curved or bent plates or profiles (generally, pipes or the like) formed of said curved plates. The coating layers and the base body are simultaneously sintered into a plate-like sintered body. Preferably, the thickness ratio of one of coating layer of $Al_2O_3$ with respect to the $ZrO_2$-base plate-like sintered body (base material) should be 1/100 to 25/100 (more preferably 1/100 to 20/100). If required, this coating layer may be formed partly or wholly over the plate-like sintered body.

According to this system, it is possible to achieve a mechanical strength higher than that of the sintered body comprising the base material alone by a factor of two or more, since the coating layer and the base material contract integrally, and interaction occurs with each other. According to this invention, the thus obtained strength exceeds that of the $Al_2O_3$-base material per se used as the coating layer. This is considered to be due to the fact that the shrinkage moduli (green dimension/dimension after sintering) of the base material and the coating layer (material) are used in varied combinations when sintering the base material onto which the coating layer has been coated. More specifically, to make the shrinkage modulus of the coating layer smaller than that of the base material would cause that the coating layer contracts to a higher extent than the original degree of contraction during sintering resulting in further densification, and that there is produced therein a compression stress. It is considered that the higher the difference in the relative ratio of the shrinkage moduli between the coating material and the base material, the greater the resulting effect, provided that the sintered body must be free from any crack, warpage, etc. Preferably, the ratio of the shrinkage moduli of the base material to that of the coating layer material should be in a range of 1.01 to 1.08. Where that ratio is lower than 1.01, no sufficient reinforcing effect is obtained. Where that ratio is higher than 1.08, on the other hand, cracks, warpage, etc. tend to occur. The coating layer is based on $Al_2O_3$, a preferable example of which is usually alpha-$Al_2O_3$ having a purity of, preferably, no lower than 90 mol %. This is derived from the concept that sufficient incorporation of thermally and chemically stable alpha-$Al_2O_3$ is preferable from the very viewpoint of reinforcing layers.

In the present invention, it is required to make the $ZrO_2$-base material and the coating layer integral and to use a densified coating material, which leads to the need of sintering the coating material at a temperature at which the base material is sintered. Therefore, it is preferred that the sintering aids are added to the coating material.

In the following, a preferred embodiment of the process for the production of the reinforced sintered bodies will be explained. Stabilizers such as $Y_2O_3$, CaO, MgO and the like are added to the starting $ZrO_2$ material in the predetermined amount (usually 4 to 10 mol %) for mixing in a ball mill, etc. After drying, the resulting mixture is calcined, and the thus calcined powder is pulverized to obtain a starting material for the base material. A binder such as organic binders is added to the base material, which is formed into a plate-like shape by means of the doctor blade, extrusion, pressing or the like technique to obtain a green substrate based on $ZrO_2$, which is partly or entirely stabilized. On the other hand, an organic binder is mixed with the starting $Al_2O_3$ material, and the resulting mixture is pasted to obtain a coating material.

The coating material is coated onto both sides of the green substrate by means of paste (screen) printing, green sheet compression bonding or thermocompression bonding, and the resulting product is sintered at 1500° to 1550° C. for 1 to 4 hours in an oxidizing atmosphere, whereby the coating (protective) layer-provided plate-like sintered body based on partly or wholly stabilized $ZrO_2$ is obtained.

According to the present invention, a bending strength higher than that of $Al_2O_3$ itself can be assured, as noted from the experimental data to be given later (in Tables 1 and 2).

Preferred embodiments are described by reference to the Drawings.

The reinforced plate-like sintered bodies of the present invention, which can be produced in this manner, may have a thickness of, ca., 0.1 to 5 mm, and can be thinner than the conventional (one-layer) product having the same strength by about 20 to 40%.

The function element based on the reinforced solid electrolyte according to the third aspect may be obtained by, for instance, providing lead layers 4 and electrodes 3 on both sides of the thus obtained reinforced solid electrolyte plate by means of one of the techniques well-known in the art such as screen printing. Alternatively, it may be contained by forming a green pattern for lead wires and electrodes on a green substrate of the aforesaid reinforced zirconia solid electrolyte, followed by simultaneous sintering. Usually, noble metal like platinum may be used for the electrodes and lead wires.

Figure 3A:
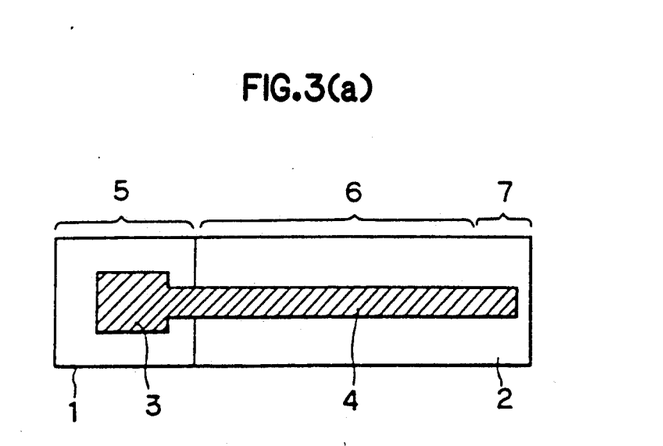
Figure 3B:
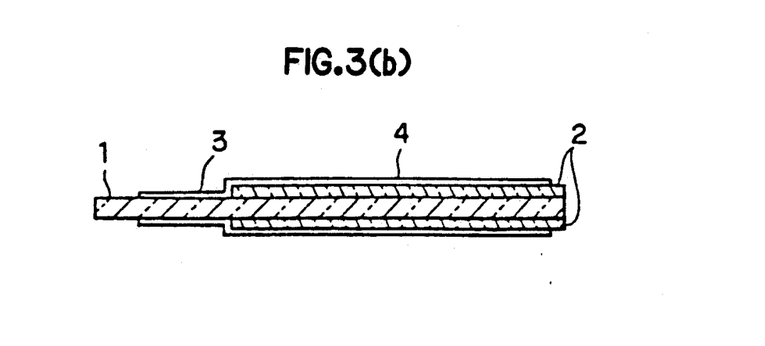

FIG. 3 is illustrative of the basic construction of the function element based on the reinforced zirconia solid electrolyte according to the present invention. In FIG. 3 the numerals 1-7 represent as follows:

1 = solid electrolyte substrate,
2 = dense alumina layer,
3 = electrode,
4 = lead layer,
5 = electrochemically operating portion.
6 = arm portion, and
7 = retaining portion.

Figures 4A, 4B:
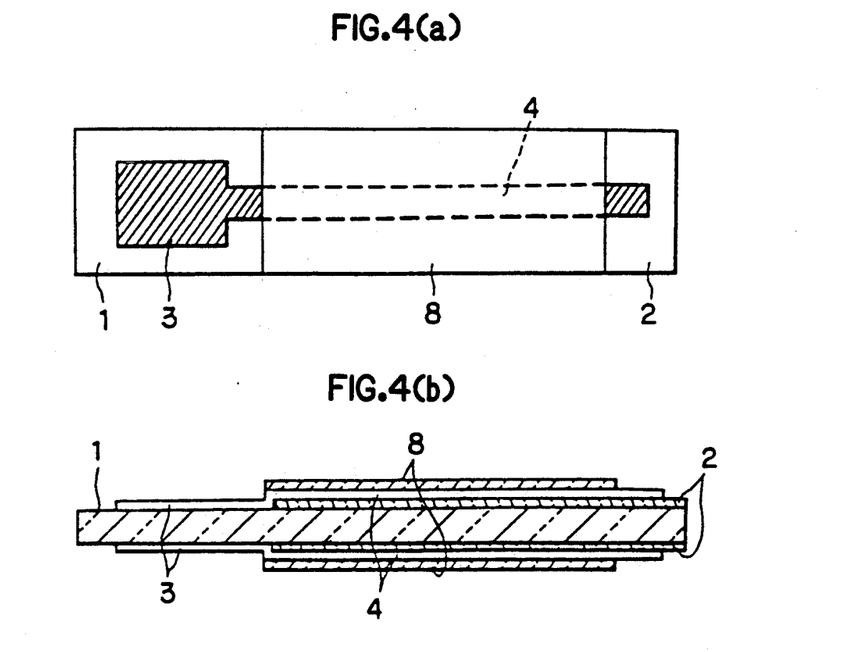
Figures 5A, 5B:
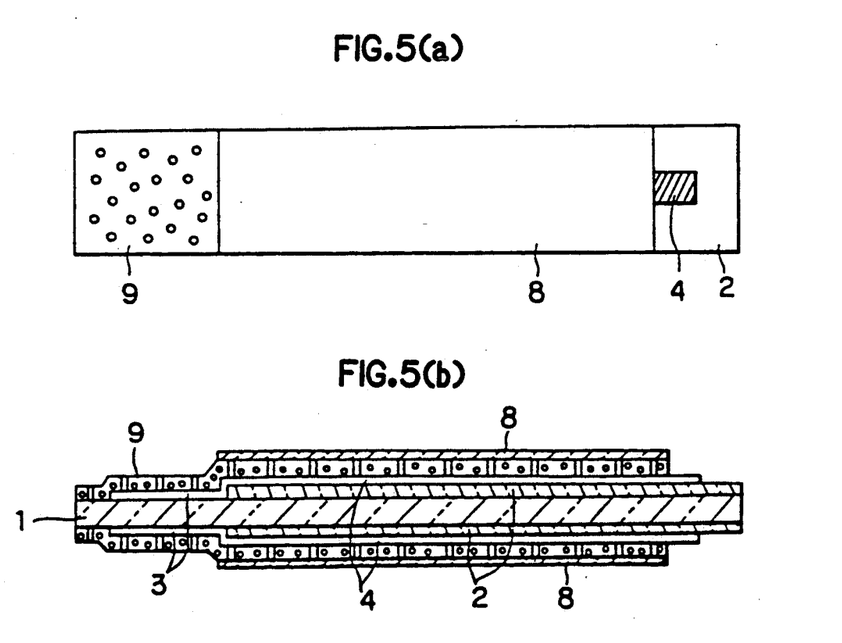
FIG. 5 shows another function element based on a reinforced zirconia solid electrolyte. It is to be noted that (a) and (b) are plan and side views, respectively.

If required, an additional dense layer of alumina 8 may be applied on the surface of the arm portion, thereby obtaining an element in which the insulating properties of the lead portion is further improved (FIG. 4(a), (b)). In addition, as shown in FIG. 5(a), (b), the provision of a porous protective layer 9 over the entire surface of the element may make the electrolde and lead portions resistant against corrosive gases, etc. The porous material may be alumina or other ceramics. A dense insulating protective layer 8, e.g., alumina may be provided on the porous protective layer 9.

The present invention is also taken as being applicable to oxygen concentration cells, oxygen pumps, etc. with additional construction means. A ceramic coating layer similar to that applied to the arm portion may be applied over the circumference and both sides of the electrochemically operable portion for further increases in the stability thereof.

EXAMPLES

The examples of the present invention will be given.

EXAMPLE 1

The first aspect of the present invention will now be explained with reference to the example. Also, the process (second aspect) for producing the reinforced plate-like sintered bodies based on partially or wholly stabilized $ZrO_2$ will be explained.

Figure 1:
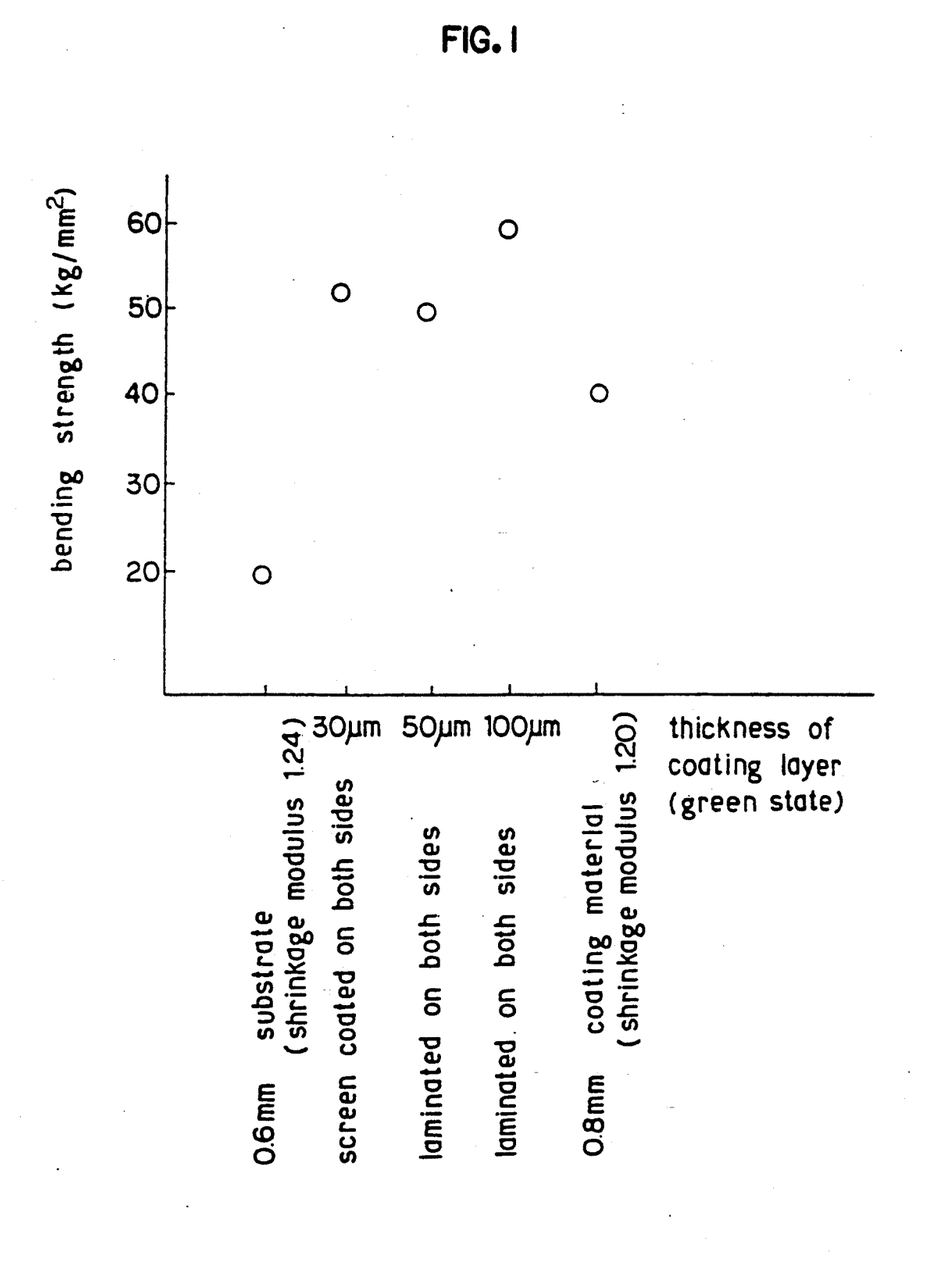
FIG. 1 shows the bending strength of a basic test piece.

Test pieces of a reinforced zirconia electrolyte provided with alumina layers coated onto both sides of a zirconia solid electrolyte substrate were prepared to measure the bending strength thereof, as stated in the following. The results are illustrated in FIG. 1.

(1) $Y_2O_3$ raw material was added to 94 mol % of $ZrO_2$ raw material having a purity of 99 % by weight and a mean particle size of 2 to 3 microns, and was mixed therewith for 5 hours in a wet manner.

(2) After drying, the resulting mixture was calcined at 1300° C. for 2 hour for pre-reaction.

(3) The sintered powders were wet-pulverized for 50 hours to obtain a substrate material.

(4) Fifteen (15) % by weight of a binder (polyvinyl butyral) were added to the substrate, and the resulting product was mixed with toluene, etc. to form a sheet-like product having a thickness of 0.7 mm.

(5) $Al_2O_3$ of 92% purity, by weight, (with the balance being impurities 5% $SiO_2$ and 2% MgO and the mean particle size being 1 to 2 microns) and an organic binder (10% by weight of polyvinyl butyral) were mixed together with a solvent acetone to form a pasty coating material. Using this paste, a sheet having a thickness of about 50 microns was also prepared.

(6) (i) The paste obtained in the step (5) was coated onto the substrate sheet by means of screen printing each 30 microns on each side). (ii) The 50 micron-thick sheet obtained in the step (5) was laminated by means of thermo compression bonding making up each 50 or 100 microns on each side). The thus prepared green material was cut into a width of 5 mm and a length of 45 mm, and was sintered at 1520° C. for 4 hours to obtain test pieces.

It has evidently been found from FIG. 1 that all the plate-like sintered bodies having on both sides the screen-printed layers of each 30 microns, the laminated layers of each 50 microns and the laminated layers of each 100 microns provide a much improved bending strength over the sintered product consisting of the substrate alone or the coating material alone. The products according to the present invention shows a strength of 50 kg/mm² even after 1000 hour-durability testing at 250° C., and exhibit excellent stability at lower temperatures. It is to be noted that a product obtained by forming a 0.25 mm-thick green sheet on a 0.35 mm-thick green sheet tore up into pieces due to crack formation after sintering.

It is to be understood that the present invention is applicable to not only the $ZrO_2$-base sintered bodies required to have strength, but also only the portion required to partly have strength. The present invention is also applicable to oxygen sensors required to have strength. Besides, a further increased reinforcing effect is attained in an electrolyte having high conductivity, say, within a range where a larger amount of the $Y_2O_3$ stabilizer is contained.

EXAMPLE 2

(1) Six (6) mol % of $Y_2O_3$ were added to $ZrO_2$ (having a mean particle size of 2 microns and a purity of 99% by weight), and an organic biner was added to the resulting product to form a sheet having generally a thickness of 0.8 mm and (partly a thickness of 0.7 mm) (hereinafter referred to as substrate I).

(2) Ten (10) mol % of an organic binder (polyvinyl butyral) were added to $Al_2O_3$ having a mean particle size of 1.5 microns (and having a purity by weight of 92% and containing 5% $SiO_2$, 2% MgO and 1 % CaO) to form a parte (coating 1) and further prepare a sheet (coating 2).

(3) Two (2) % by weight (to 5 % by weight) of $ZrO_2$ having a mean particle size of 2 microns and a purity by weight of 99% were added to the paste material to form a paste (coating 3).

(4) The substrate I was coated on both sides with the coating 1 into a thickness of about 60 microns by means screen printing. The substrate I was also laminated with the coating 2 by means of thermo-compression bonding (at 80° C.).

(5) Removal of resins was effected at 250° C. for 10 hours. These samples were cut into a width of 5 mm and a length of 45 mm, and sintered at 1520° C. for 4 hours. The sintered samples were subjected to three-point bending test at a span of 18 mm. Similar results were obtained as set forth in Tables 1 and 2, i.e., test piece Nos. 7-12 of Table 1, Nos. 27-31 of Table 2.

EXAMPLE I

1. Ten (10) % by weight of an organic binder (polyvinyl butyral) were added to an $Al_2O_3$-base material having a mean particle size of 1.5 microns (having a purity, by weight, of 92% and further containing 5% $SiO_2$, 2% MgO and 1% CaO) to form a sheet having a thickness of 0.8 mm (designated as Substrate I).

2. Two (2) % by weight of $ZrO_2$ having a mean particle size of 2 microns and a purity of 99% by weight were added to the composition of the Substrate I to prepare a paste (coating 1) and a sheet (coating 2).

3. The coating 1 was screen-printed on one side of the Substrate I into a thickness of about 30 microns. The coating 2 was also laminated on the Substrate I by means of thermocompression bonding.

4. Removal of resins was effected at 250° C. for 10 hours.

5. For the purpose of comparison, a paste (coating 3) and a sheet (coating 4) were formed of the composition of the Substrate I in steps similar to the steps 3 and 4.

The coating 6 was also laminated on the Substrate II by means of thermocompression bonding (at 80° C.).

4. Removal of resins was effected at 250° C. for 10 hours. These samples were cut into a width of 5 mm and a length of 45 mm, and sintered at 1520° C. for 4 hours in the atmosphere. The sintered products were subjected to bending testing at a span of 18 mm in the three-point supporting manner. The results are set forth in Table 1 and 2.

TABLE 1

| Test Piece No. | | Structure | | Thickness of Green Coating*/ Thickness of Green Substrate | Bending Strength kg/mm$^2$ | Remarks | Range |
|---|---|---|---|---|---|---|---|
| Example I | 1 | Substrate I Alone | | 0/0.8 | 42 | — | A[1)] |
| Shrinkage | 2 | Coating 2 Alone | | 0.8/0 | 42 | — | A |
| Modulus Substrate | 3 | Substrate I + Coating 1 | One Side | 0.03/0.8 | 52–64 | — | A |
| 1.198 Coating | 4 | Substrate I + Coating 2 | One Side | 0.10/0.8 | 50–58 | — | A |
| Layer 1.185 | 5 | Substrate I + Coating 2 | " | 0.40/0.8 | 45–50 | Large Warpage | A |
| | 6 | Substrate I + Coating 3,4 | " | 0.03/0.8 0.10 | 40–48 | — | A |
| Example II | 7 | Substrate II Alone | | 0/0.8 | 18–21 | — | A |
| Shrinkage Modulus Substrate | 8 | Substrate II + Coating 5 | One Side | 0.06/0.8 | 50–55 | Small Warpage Produced | A |
| 1.245 Coating | 9 | Substrate II + Coating 5 | Both Sides | 0.12/0.8 | 53–60 | — | B |
| Layer 1.198 | 10 | Substrate II + Coating 6 | One Side | 0.20/0.8 | Large Warpage, No Measurement | | A |
| | 11 | Substrate II + Coating 6 | Both Sides | 0.40/0.8 | 51–63 | — | B |
| | 12 | Substrate II + Coating 6 | " | 0.55/0.5 | Cracks | — | A |

[1)]A: out of the claimed scope
[2)]B: within the claimed scope
*sum of both sides

TABLE 2

| Test Piece No. | Ratio of Shrinkage Modulus $l_0/l_1$ Subst./Coat. | Shrinkage Modulus $l_0/l_1$ | | Bending Strength kg/mm$^2$ | Thickness of Green Coating*/ Thickness of Green Substrate mm/mm | Structure | Range |
|---|---|---|---|---|---|---|---|
| 27 | 1.05 | Substrate Coating | 1.245 1.185 | 55–65 | 0.06/0.7 | Substrate II + Coating 1/Both Sides | B |
| 28 | 1.064 | Substrate Coating | 1.275 1.198 | 30–35 | 0.06/0.7 | Substrate III + Coating 5/Both Sides | B |
| 29 | | | | 20–25 | 0/0.9 | Substrate III Alone | A |
| 30 | 1.087 | Substrate Coating | 1.302 1.198 | About 65** | 0.06/0:75 | Substrate IV + Coating 5/Both Sides | A |
| 31 | | | | About 65 | 0/0.75 | Substrate IV Alone | A |

*Total value of both coatings
**Crackings easily occur due to snake like deformation in transverse direction of the substrate plane
In Table 2, Substrate III: Y$_2$O$_3$ 8 moles $l_0/l_1$ = 1.275
Substrate IV: Y$_2$O$_3$ 4 moles $l_0/l_1$ = 1.302
(Substrate IV contains a total of 8 wt. % of Al$_2$O$_3$, Silica, etc.)
It is noted that the substrate (IV) containing less than 5 mol % of Y$_2$O$_3$ tends to be reduced in bending strength to about ½ after 1000 hr-durability testing at a temperature of 700° C. or less.
A: out of the claimed scope
B: within the claimed scope

EXAMPLE II

1. Six (6) mol % of Y$_2$O$_3$ were added to the starting ZrO$_2$ material (having a mean particle size of 2 microns and a purity of 99% by weight), followed by the addition of an organic binder, to thereby prepare a sheet having a thickness of 0.8 mm (designated as Substrate II).

2. Of the material of Example I-1 a paste (coating 5) and a sheet (coating 6) were formed.

3. The coating 5 was screen-printed on both sides of the Substrate II into a thickness of about 30 microns.

The inventive products are improved in strength over those outside the claimed scope. This is because there is a considerable difference in the contraction due to sintering between the base material (substrate) and the coating material. Since warpage, etc. occur in the event that such a difference is large, better results are obtained when the coating layer have a small thickness.

EXAMPLE 3

Preparation of Test Piece 31

(1) Six (6) mol % of $Y_2O_3$ (having a mean particle size of 0.5 to 1 microns and a purity of no less than 99.9%) were added to $ZrO_2$ raw material (having a mean particle size of 1 to 2 microns and a purity of no less than 99%), and were wet-mixed therewith for 5 hours in a ball mill. After drying, the resulting mixture was calcined at 1300° C. for 2 hours. The thus sintered powders are wet-pulverized for 50 hours in a ball mill to obtain the starting powders for a zirconia solid electrolyte, 80% or more of which are no higher than 25 microns.

(2) The starting powders were mixed with a binder and a solvent to obtain a slurry, which was then formed into a sheet having a given thickness (about 0.8 mm) by the doctor blade technique.

(3) As the starting material for coating layers, use was made of $Al_2O_3$ (92% by weight, the remainder being impurities mainly MgO; particle size=90% is less than 2.5 microns). An organic binder and a solvent butyl carbidol were mixed in that starting material to prepare a paste.

(5) With the use of screen printing, the sheet obtained in the step 2 was screen-printed on its both sides with the paste for alumina coating obtained in the step (4) into a thickness of 30 microns.

(6) For the measurement of mechanical strength, the thus obtained product was cut into a width of 5 mm and a length of 45 mm, and was thereafter sintered at 1520° C. for 4 hours in the atmosphere to prepare a zirconia-base solid electrolyte plate (having a thickness of 0.65 mm), on both sides thereof including dense alumina coating layers of about each 25 microns in thickness.

Preparation of Test Pieces 32-1 and 32-2

In order to provide platinum layers on the dense alumina coating layers of the test piece 31, the starting material for such layers were prepared in the following manner.

Five (5) parts by weight of the zirconia solid electrolyte material were added as the co-matrix to 100 parts by weight of platinum (black : sponge=2 : 1), and an organic binder and a solvent butyl carbidol were further added to obtain a paste for the platinum layers.

(8) This was screen-printed on one or both sides of the sheet obtained in a step similar to the step (5) for the test piece 31 into a thickness of 15 or 30 microns (the thickness of the alumina paste to which the platinum paste is to be applied was about 15 microns).

(9) After cut into a width of 5 mm and a length of 45 mm, this was sintered at 1520° C. for 4 hours in the atmosphere to obtain a zirconia-base solid electroyte plate (having a thickness of 0.65 mm) of a multi-layer structure that has on its each side a dense alumina layer of each about 10 microns in thickness and an about 25 micron-thick platinum layer contiguous thereto. This is designated as the test piece 32-1. Prepared was also a plate having on one side a 10 micron-thick dense alumina layer and an about 25 micron-thick platinum layer contiguous thereto and on the other side a 25 micron-thick dense alumina layer alone. This is designated as the test piece 32-2.

Preparation of Test Piece 33

(10) By a step similar to the step (5) for the test piece 31, an alumina paste was screen-printed on one side alone.

(11) After having cut into a width of 5 mm and a length of 45 mm, this was sintered at 1520° C. for 4 hours in the atmosphere to prepare a zirconia-base solid electrolyte plate (having a thickness of 0.65 microns) having on one side alone an about 25 micron-thick dense alumina coating layer.

Preparation of Test Piece 35

(16) After having cut into a width of 5 mm and a length of 45 mm, the sheet obtained in the step (2) for the test piece 31 was sintered at 1520° C. for 4 hours in the atmosphere to prepare a simple zirconia electroyte plate (having a thickness of 0.65 mm).

Preparation of Test Piece 36

(17) The paste obtained in the steps (3) and (4) in the test piece 31 was formed into an alumina sheet having a thickness of about 0.8 mm by means of the doctor blade technique.

(18) After having cut into a width of 5 mm and a length of 45 mm, this was sintered at 1520° C. for 4 hours in the atmosphere to prepare a simple alumina plate (having a thickness of 0.65 mm).

The bending strength, at normal temperature, of the thus prepared test pieces was measured at a span of 18 mm in the three-point supporting manner. The results are set forth in Table 3.

TABLE 3

| Test Piece No. | S. M. ($l_0/l_1$) Substrate | S. M. ($l_0/l_1$) Coating | Ratio of S. M. | Bending Strength (kg/mm²) | Range |
|---|---|---|---|---|---|
| 31 | 1.245 | 1.198 | 1.039 | 45–65 | B |
| 32-1 | " | " | " | 50–65 | B |
| 32-2 | " | " | " | 50–65 | B |
| 33 | " | " | " | 45–60* | A |
| 34 | " | porous | — | 17–25 | A |
| 35 | "** | — | — | 17–20 | A |
| 36 | "*** | — | — | 40–45 | A |

*Slight warpage produced
**$ZrO_2$ Substrate
***$Al_2O_3$ Coating
A: Out of the claimed scope
B: Within the claimed scope

EXAMPLE 4

Figure 2A:
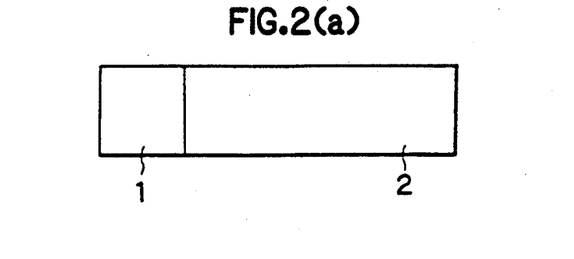
FIGS. 2 to 4 illustrate a function element based on a reinforced zirconia solid electrolyte (No. 41), in which electrode and lead layers are formed on the reinforced zirconia solid electrolyte substrate having dense layers of alumina on both sides thereof.
Figure 2B:
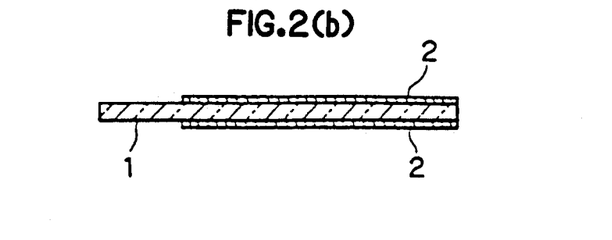

A sheet having a thickness of 0.8 mm was prepared from a zirconia solid electrolyte material (containing 6 mol % of $Y_2O_3$), which was the same as in the step (1) for the aforesaid test piece 31 by the doctor blade technique, and was cut into width of 10 mm and a length of 50 mm. As illustrated in FIG. 2, the alumina paste obtained in the steps (3) and (4) for the aforesaid test piece 31 was screen-printed over the entire surface of that sheet, except for the leading or free end portion of 10 mm in length, into a thickness of 15 microns.

Next, this sheet was screen-printed on both its sides into a thickness of 30 microns with the platinum paste used for the step (7) for the aforesaid test piece 32 in such a manner that electrodes (of 2 mm in width) were formed on the leading end portions free from any alumina paste, and a lead portion (of 1.0 mm in width) was formed, extending from the electrodes and terminating on the retaining end portion to be fixed on which the alumina paste had been printed (FIG. 3).

The same alumina paste was screen-printed on the alumina plate already printed on the aforesaid sheet into a thickness of 30 microns, provided, however, that the end of the lead was partly exposed to view on the retaining end portion (FIG. 4).

Figure 6:
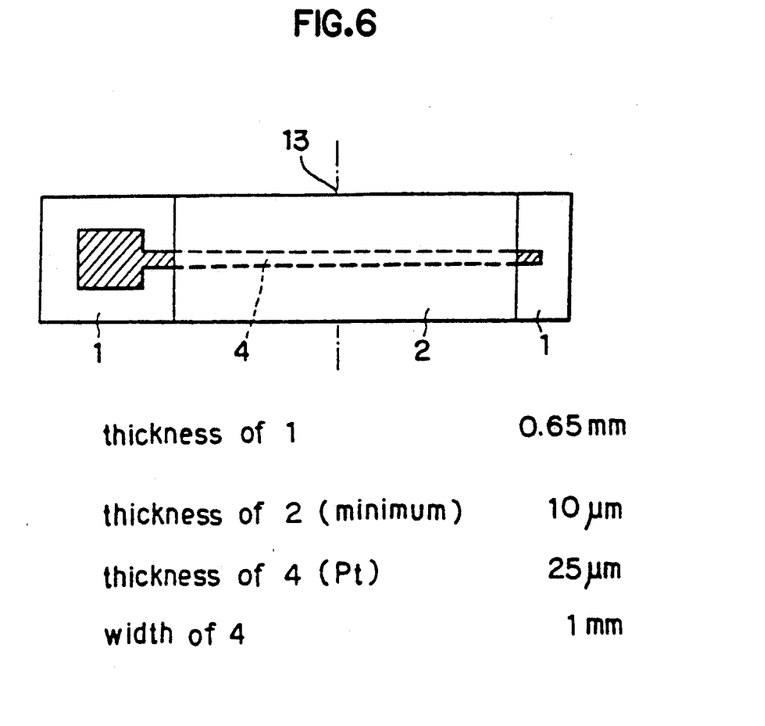
FIG. 6 and 7 illustrate the method for measuring the bending strength values as specified in Table 2.

This was sintered at 1520° C. for 4 hours in the atmosphere to prepare a function element (No. 1) of a size shown in FIG. 6, which is for instance suitable for use in a incomplete combustion sensor.

On the other hand, sawdust was incorporated into the alumina paste obtained in the steps (3) and (4) for the test piece 31 as the organic coarse particles for forming through-pores therein after sintering. The resulting sawdust-containing alumina paste was screen-printed on the entire surface of the intermediate product as illustrated in FIG. 3. Furthermore, the alumina paste obtained in the steps (3) and (4) for the aforesaid test piece 31 was screen-printed on the portion of the aforesaid intermediate product, except for the electrode-attached part or the electrochemically operable part, into a thickness of 30 microns, to thereby obtain a function element (No. 2) as illustrated in FIG. 5.

For the purpose of comparison, first and second control function elements (Nos. 3 and 4) were prepared. The first control element (No. 3) was made under the conditions equivalent to the function element No. 1, provided, however, that the zirconia-base solid electrolyte sheet was printed directly with platinum electrodes and a lead portion therefor, and no printing of an alumina paste for the dense alumina layer was effected on its one side. The second control element (No. 4) was made under the equivalent conditions, provided however that the zirconia-base solid electrolyte sheet was printed directly with platinum electrodes and a lead portion therefor, and no printing of alumina paste for the dense alumina layer was effected on both sides of the electrolyte sheet.

Figure 7:
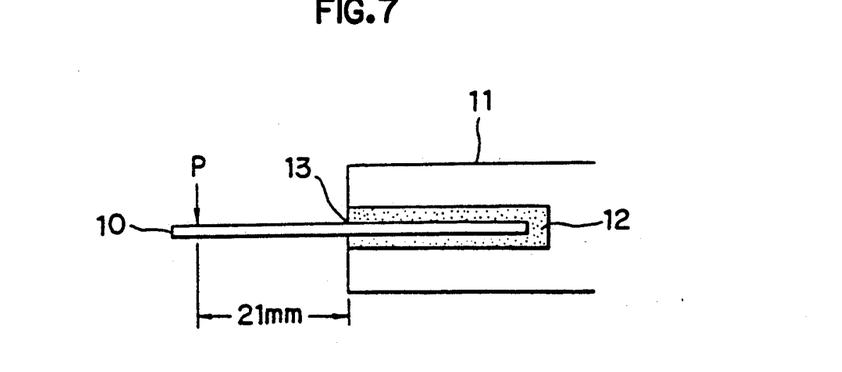

The function elements 10 according to the aforesaid two examples and the control function elements were fixedly inserted into an elongate slot in a fitting member 11 for fixation through an adhesive layer (alumina cement 12), leaving the portions extending from the extremities by 25 mm as the free ends, as illustrated in FIGS. 6 and 7. In FIG. 6, "1" represents the zirconia-base solid electrolyte substrate, "2" dense alumina protective layer, and "4" lead portion, respectively. The middle portion, viz., the portion spaced away from the fulcrum 13 by 21 mm was bent perpendicularly with respect to the plate to determine the force P upon fracture The results are set forth in Table 4.

Further, function element Nos. 5, 6 were produced by the abovementioned process, provided that their zirconia substrates were ones which have been produced by using starting $ZrO_2$ raw material calcined at 1340° C. (element No. 5) or 1380° C. (element No. 6) in the step (1) for the aforesaid test piece 31.

Furthermore, function element Nos. 7-9 were produced by the abovementioned process, provided that their zirconia substrates were ones in which five (5) mol % of $Y_2O_3$ were added in the step (1) for the aforesaid test piece 31, and their $Al_2O_3$ coating layers were ones having lower green-density in which the organic binder and a solvent butyl carbidol were mixed in turn in a greater amount than that in the step (3) for the aforesaid test piece 31.

TABLE 4

| Element No. | S. M. ($l_0/l_1$) Substrate | S. M. ($l_0/l_1$) Coating | Ratio of S. M. | P (kg) | Range |
|---|---|---|---|---|---|
| 1 | 1.245 | 1.198 | 1.039 | 0.5–0.7 | B |
| 2 | 1.245 | 1.198 | 1.039 | 0.55–0.75 | B |
| 3* | 1.245 | 1.198 | 1.039 | 0.4–0.6*** | A |
| 4** | 1.245 | — | — | 0.2–0.3 | A |
| 5 | 1.240 | 1.198 | 1.035 | 0.5–0.65 | B |
| 6 | 1.232 | 1.198 | 1.028 | 0.45–0.6 | B |
| 7 | 1.257 | 1.228 | 1.024 | 0.45–0.6 | B |
| 8 | 1.257 | 1.246 | 1.009 | 0.35–0.5 | A |
| 9 | 1.257 | 1.253 | 1.003 | 0.3–0.45 | A |
| 10** | 1.257 | — | — | 0.3–0.4 | A |

*One side coating
**No coating
***large warpage
A Out of the claimed scope
B Within the claimed scope From the tables, it is found that the mechanical strength of the zirconia solid electrolyte-function elements are significantly reinforced.

As explained above, since the zirconia solid electrolyte-function elements according to the present invention have excellent mechanical strength, it is unlikely that breaking accidents may arise during processing or assembling, or in use. Due to the fact that the lead wire is provided on the alumina insulating layer, the insulating properties of the lead portion are improved.

The illustrated embodiments have one retaining portion, however a plurality of retaining portions may be provided, too. On the other hand, a plurality of electrochemically operating portions may be provided, too. In the all any modification based on the gist of the present invention may be made without departing from the gist herein disclosed and claimed in the accompanying claims.

What is claimed is:

1. A zirconia-base solid electrolyte function element comprising a zirconia-base solid electrolyte substrate, the substrate including at its free end an electrochemically operable portion provided with an electrode on each side of the substrate, another portion to be retained, and an arm portion defined by an intermediate portion between the free end and said another portion, wherein a reinforcing layer is formed directly on each side of said zirconia-base solid electrolyte substrate, the reinforcing layers extending at least from said arm portion to said another portion to be retained, the ratio of the shrinkage modulus of the zirconia-base electrolyte substrate to the reinforcing layers being 1.02 to 1.08, the thickness ratio of each of said reinforcing layers to said zirconia-base solid electrolyte substrate is 1/100 to 25/100, and the substrate and reinforcing layers having been sintered simultaneously.

2. A function element as defined in claim 1, in which the ratio of the shrinkage moduli of said zirconia-base electrolyte substrate to the reinforcing layers is 1.02 to 1.06.

3. A function element as defined in claim 1, in which the ratio of the shrinkage moduli of said zirconia-base electrolyte substrate to the reinforcing layers is 1.03 to 1.05.

4. A function element as defined in claim 1, in which the thickness ration of said reinforcing layers to said zirconia-base electrolyte substrate is 5/100 to 15/100.

5. A function element as defined in claim 1, in which said zirconia-base solid electrolyte substrate has a thickness of 0.1 to 5 mm.

6. A function element as defined in claim 5, in which said zirconia-base solid electrolyte substrate has a thickness of 0.1 to 2 mm.

7. A function element as defined in claim 1, in which said ceramic material is alpha-alumina.

8. A function element as defined in claim 1, in which said zirconia-base solid electrolyte is wholly or partially stabilized primarily by yttrium oxide.

9. A function element as defined in claim 1, in which the reinforcing layer is formed on a portion to be strengthened of the substrate.

10. A function element as defined in claim 1, in which the reinforcing layer is formed on the electrochemically operable portion except for the electrode portion.

11. A function element as defined in claim 1, in which the bending strength of the substrate has been substantially increased over the bending strength of the substrate when sintered alone.

12. A function element as defined in claim 11, in which the bending strength has been increased by at least 50%.

13. A function element as defined in claim 11, in which its bending strength has been increased by at least 70%.

14. A function element as defined in claim 1, in which a lead portion connected with the electrode is formed on the surface of said reinforcing layer.

* * * * *